(12) United States Patent
Staton et al.

(10) Patent No.: US 7,818,129 B2
(45) Date of Patent: Oct. 19, 2010

(54) DETECTION OF FEATURE BOUNDARY PIXELS DURING ARRAY SCANNING

(75) Inventors: Kenneth L. Staton, San Carlos, CA (US); John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 885 days.

(21) Appl. No.: 10/912,463

(22) Filed: Aug. 4, 2004

(65) Prior Publication Data
US 2006/0031025 A1 Feb. 9, 2006

(51) Int. Cl.
*G06G 7/58* (2006.01)
*G01N 33/483* (2006.01)
*C12Q 1/68* (2006.01)

(52) U.S. Cl. .............................. 702/19; 703/11; 700/30; 435/6

(58) Field of Classification Search ........................ None
See application file for complete search history.

(56) References Cited

U.S. PATENT DOCUMENTS

| | | | |
|---|---|---|---|
| 4,908,875 A * | 3/1990 | Assael et al. ................ 382/272 |
| 5,770,456 A * | 6/1998 | Holmes ....................... 436/518 |
| 6,674,882 B1 | 1/2004 | Shams | |
| 2003/0165871 A1 | 9/2003 | Corson et al. | |
| 2003/0168579 A1 | 9/2003 | Corson et al. | |
| 2003/0203371 A1 | 10/2003 | Corson et al. | |
| 2004/0021911 A1 | 2/2004 | Corson et al. | |
| 2004/0023224 A1 | 2/2004 | Corson et al. | |
| 2004/0064264 A1 | 4/2004 | Corson et al. | |

OTHER PUBLICATIONS

Glasbey et. al., 2003, Combinatorial image analysis of DNA microarray features, Bioinformatics, 19(2), 194-203.*
Cheung et al. "Making and Reading Microarrays" Nature America Inc—Nature Genetics Supplement (1999) 21:15-18.

* cited by examiner

*Primary Examiner*—Marjorie Moran
*Assistant Examiner*—Larry D Riggs, II

(57) ABSTRACT

Methods for identifying feature boundary pixels are provided. In general, the subject methods involve evaluating a pixel signal to identify any difference in amplitude between a first part of the signal and a second part of the signal. If the difference is significant, the pixel signal may be indicated as a pixel representing a feature boundary. Also provided are systems and programming for performing the subject methods, and an array scanner containing these systems and programming.

21 Claims, 2 Drawing Sheets

DETECTION OF FEATURE BOUNDARY PIXELS DURING ARRAY SCANNING

BACKGROUND OF THE INVENTION

Arrays of surface-bound binding agents may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One representative array assay method involves biopolymeric probes immobilized in an array on a substrate, such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In certain instances, the target molecules are labeled with a detectable tag such as a fluorescent tag or chemiluminescent tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

For each pixel of a scan, a detector (e.g., photodetector such as a photomultiplier tube) may detect light emitted from the surface of a microarray, and output an analog signal line that changes in amplitude according to the amount of emitted light entering the detector. This analog signal is usually sampled and digitized using an analog-to-digital converter (A/D converter) and integrated using a digital signal processor (DSP) to provide data, e.g., a numerical evaluation of the brightness of the pixel. This data is usually stored and analyzed at a later date.

During data analysis, signals for pixels of each feature of an array are integrated to provide an evaluation of the level of target bound to each feature of the array. A critical step in the analysis of raw array data, therefore, is identifying which pixels represent features (i.e., which features are "feature pixels"), and which pixels do not represent features (and are therefore represent "background" pixels). Accordingly, there is a need for improved methods for identifying feature pixels, in order to increase the accuracy and reliability of processed array data.

The present invention meets this, and other, needs.

Literature of interest includes: U.S. Pat. No. 6,674,882, published U.S. patent applications: 20030168579, 20030165871, 20040064264, 20040023224, 20040021911, 20030203371 and 20030168579; and Cheung et al., Nature Genetics 1999, 21: 15-19.

SUMMARY OF THE INVENTION

Methods for identifying feature boundary pixels are provided. In general, the subject methods involve evaluating a pixel signal to identify any difference in amplitude between a first part of the signal a second part of the signal. If the difference is significant, the pixel signal may be indicated as a pixel representing a feature boundary. Such a pixel may be used to identify the perimeter of features. Also provided are systems and computer programming products for performing the subject methods, and an array scanner containing these systems and programming products. The subject invention finds use in a variety of different applications, including both genomics and proteomics applications.

In one embodiment, the invention provides a method of determining whether a pixel signal produced during scanning of a chemical array (e.g., a nucleic acid or polypeptide array) is a feature boundary pixel signal, comprising: evaluating change in amplitude of said pixel signal (to provide, in certain embodiments a numerical evaluation); wherein a pixel signal having a significant change in amplitude is a feature boundary pixel signal. Certain embodiments of this method comprise evaluating any difference in amplitude between a first part of the signal and a second part of the signal to provide an evaluation of amplitude change of the pixel. In certain embodiments, a pixel signal having a change in amplitude above a pre-determined level indicates that the signal is a feature boundary pixel signal.

In one embodiment, a pixel signal having a line of best fit having a slope greater than a threshold slope indicates that said pixel is a feature boundary pixel. In this embodiment, the method may comprise evaluating closeness of the pixel signal to its line of best fit.

Any evaluation produced by the subject method may be stored on a computer readable medium.

The method may further comprise integrating the pixel signal to produce, for example, a numerical evaluation of the pixel. Such a numerical evaluation may be stored on a computer a readable medium.

In certain embodiments, the numerical evaluation of the pixel is adjusted if the pixel is a feature boundary pixel, or, in alternative embodiments, the numerical evaluation of the pixel is annotated with information indicating an adjustment factor for adjusting the numerical evaluation if the pixel is a feature boundary pixel.

In certain embodiments, the method further comprises indicating which end of the pixel signal represents signal from a feature area or which end of said pixel signal represents signal from a non-feature area if said pixel is a feature boundary pixel.

In certain embodiments, the method further comprises indicating where in the pixel signal transition between signal from a feature area and signal from a non-feature area occurs if the pixel is a feature boundary pixel.

The method may comprise scanning a chemical array to provide the pixel signal.

In another embodiment, the invention provides method of evaluating a feature on a surface of a chemical array, comprising: scanning the feature to provide a plurality of pixel signals for the feature; integrating pixel signals to provide numerical evaluations of the pixels; and adjusting the numerical evaluations using the adjustment factor discussed above.

The invention also provides a computer-readable medium comprising: programming for execution by a digital signal processor to produce data for a pixel in a scan of a chemical array, comprising: instructions for evaluating change in amplitude of said pixel signal, to produce data for said pixel. The computer readable medium may also comprises programming to integrate said pixel signal. The computer-readable medium may provide for a signal processor output that is a multi-bit code, in which a first part of said code represents an evaluation of amplitude any amplitude change of said signal and a second part of said code represents said integrated signal. The computer-readable medium may be contained in a computer, and a computer containing the computer-readable medium may be comprised by or in communication with a molecular array scanner.

In a further embodiment, the invention provides a system for performing the above-described method. In one aspect, the system comprises a chemical array scanner comprising: a laser excitation system and a photodetection system that produces a signal representative of emitted light (e.g., fluorescent light) from the surface of an array. In another aspect, the system further comprises a storage medium for storing data for a pixel in a scan of a chemical array, e.g., such as obtained from executing programming of a computer-readable medium as described above.

The invention also provides a method of assaying a sample which comprises: contacting a sample with a chemical array of two or more features immobilized on a surface of a solid support; and (b) reading the array with a chemical array scanner t to obtain data relating to a feature boundary pixel signal as described above. The invention also provides a method including transmitting a result obtained from any of the above-described methods from a first location to a remote location, and a method including receiving data representing data obtained by any of the above-described methods.

The invention also provides a kit for use in a chemical array optical scanner, comprising a computer-readable medium according to the above; and at least one chemical array.

In any of the above embodiments, the chemical array may be a biopolymer array, e.g., such as a nucleic acid or polypeptide array.

DEFINITIONS

Figure 1:
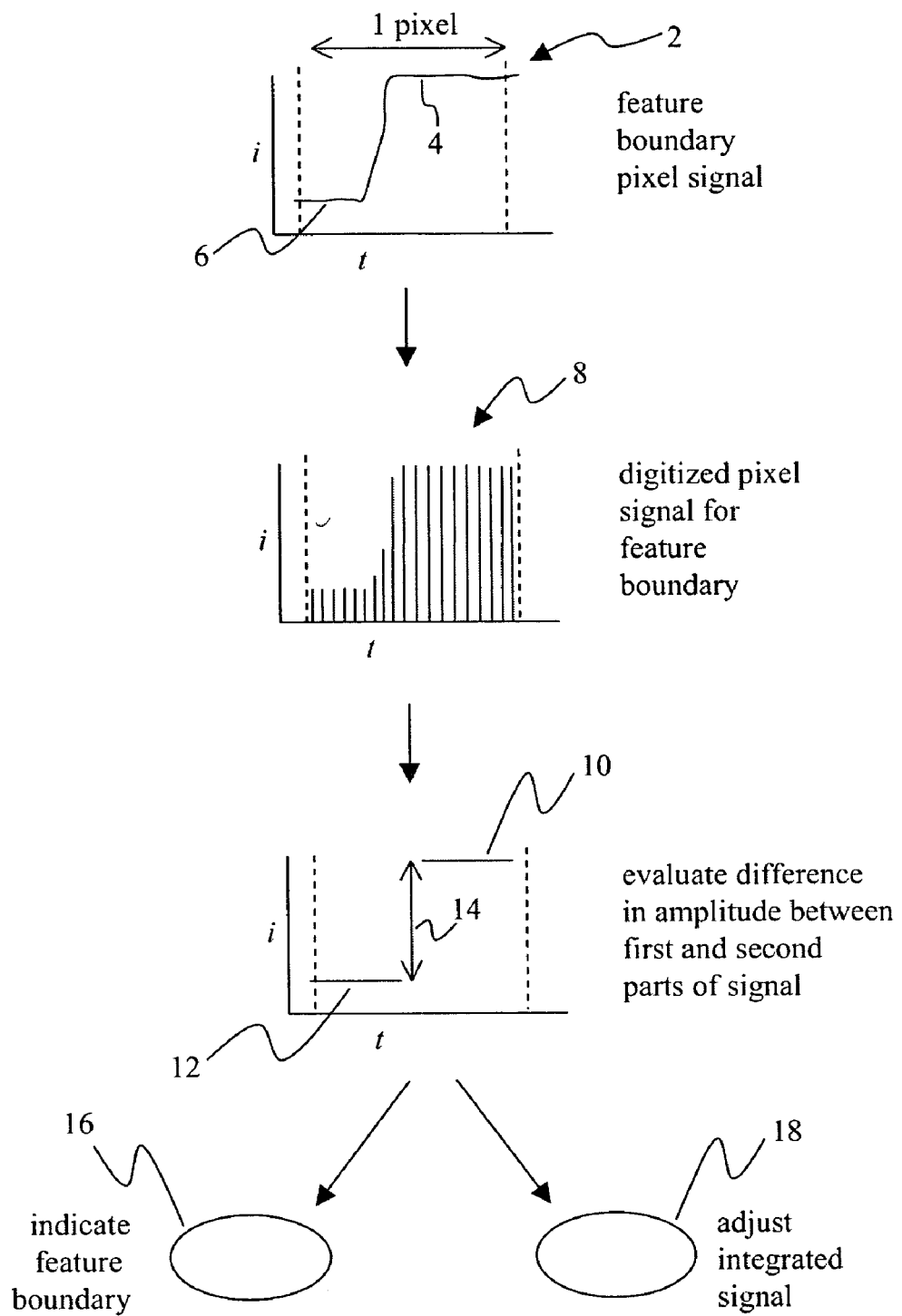
FIG. 1 schematically illustrates many general features of the invention described herein.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), polypeptides (which term is used to include peptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," or "chemical array" includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). If a device is "in communication with" another device, the devices are capable of transmitting or data or instructions to each other. Such devices may be networked to each other. "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are usually referred to in the art as "pixels". Arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

In certain embodiments, the scanner used for the evaluation of arrays includes a scanning fluorometer. A number of different types of such devices are commercially available from different sources, such as such as Perkin-Elmer, Agilent, or Axon Instruments, etc., and examples of scanners are described in U.S. Pat. Nos. 5,091,652; 5,760,951, 6,320,196 and 6,355,934.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of pixel signal to determine the brightness of a corresponding area present on the surface of an object scanned.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may programmed or hard wired to perform one or more mathematical functions, such as those described below. In certain embodiments, a signal processor may "integrate" a set of digital signals (e.g., a set of digital signals representing an analog signal or a digitized version of an analog signal). By "integrating" is meant that a set of digital signals is input into a signal processor and the signal processor provides an output signal, in certain embodiments a single output signal, that represents the set of input signals. In many embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled) prior to integration. For example, if an analog signal for a pixel is to be integrated, the signal is first sampled and digitized to provide a set of digital signals, and those digital signals are integrated by a signal processor to provide an output signal, typically a binary signal, that represents a numerical evaluation of the overall magnitude of the input set of digital signals (thereby providing a numerical evaluation of the magnitude of the analog signal for the pixel). The output of a signal processor may be referred herein as "data", and may be stored in memory.

Data from reading an array may be raw data (such as fluorescence intensity readings for each feature in one or more color channels, or, for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

A "feature boundary pixel signal" is the signal of a pixel representing a feature boundary, e.g., a signal of a pixel that transitions the boundary between a feature area and a non-feature area of an array.

In certain embodiments that will be described in greater detail below, data obtained from a feature boundary pixel signal may be associated with an "adjustment factor", where an "adjustment factor" is a value by which the data may be adjusted (e.g., multiplied by or added to) to provide a more accurate evaluation of the pixel. In certain embodiments, an adjustment factor represents the difference between data produced by integrating a pixel signal that is part feature signal and part non-feature signal, and data produced by integrating the same pixel signal, correcting for the reduced magnitude of the non-feature signal. For example, a numerical evaluation of a pixel signal that is 50% feature signal and 50% non-feature signal may be adjusted (e.g., multiplied) by an adjustment factor of 2 to provide a more accurate evaluation of the pixel. Similarly a numerical evaluation of a pixel signal that is 25% feature signal and 75% non-feature signal may be adjusted (e.g., multiplied) by an adjustment factor of 4 to provide a more accurate evaluation of the pixel.

The term "using" has its conventional meaning, and, as such, means employing, e.g. putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "providing" encompasses such terms as "generating", "identifying" and "producing".

DETAILED DESCRIPTION OF THE INVENTION

Methods for identifying feature boundary pixels are provided. In general, the subject methods involve evaluating a pixel signal to identify any difference in amplitude between a first part of the signal a second part of the signal. If the difference is significant, the pixel signal may be indicated as a pixel representing a feature boundary. Such a pixel may be used to identify the perimeter of features. Also provided are systems and programming for performing the subject methods, and an array scanner containing these systems and programming. The subject invention finds use in a variety of different applications, including both genomics and proteomics applications.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, system and methods aspects of the invention are first described. This discussion is followed by a description of suitable hardware for use in the invention.

The following U.S. patent applications are herein incorporated by reference in their entireties for all purposes: 10/912,661, entitled: "Methods and Compositions for Assessing Partially Saturated Pixel Signals", filed Aug. 4, 2004; 10/912,427, entitled: Multi-Gain Photodetection System for Array Analysis, filed Aug. 4, 2004; and 10/912,027, entitled: "Filtering of Pixel Signals During Array Scanning", filed Aug. 4, 2004. The following published U.S. patent applications are incorporated by reference in their entirety, including all definitions, for all purposes: 10/086,932 (filed on Feb. 28, 2002 and published as 20030165871), 10/261,563 (filed on Sep. 30, 2002 and published as 20040064264), 10/212,191 (filed on Jul. 31, 2002 and published as 20040023224), 10/210,848 (filed on Jul. 31, 2002 and published as 20040021911), 10/137,658 (filed on Apr. 30, 2002 and published as 20030203371) and 10/086,658 (filed on Feb. 28, 2002 and published as 20030168579).

Methodology

As mentioned above, the invention provides methods for identifying feature boundary pixels produced during scanning of a chemical array. These methods generally take advantage of the fact that during the scanning process, the detector of a scanner is usually in continuous or near continuous motion relative to the array being scanned. Accordingly, as the detector "passes over" (i.e., detects while moving relative to) a boundary for a light-emitting feature, the light signal detected by the detector usually increases from background (corresponding to a non-feature area) to non-background signal (corresponding to a light-emitting feature), or vice versa. Accordingly, a signal line (e.g., a series of individual data samples that are integrated to form a pixel) for a pixel representing the boundary for a light-emitting feature usually contains at least two parts, a first part (at either of the two ends of the signal line) corresponding to background, and a second part (at the other end of the signal line) corresponding to a feature. The signal line between these two parts of the signal usually represents the feature boundary. In certain cases, a feature boundary may span more than one pixel, e.g., two or more pixels. In these cases, signals for feature boundary pixels usually exhibit a marked increase or decrease in amplitude in signal over the time of the pixel. In contrast to a pixel signal representing a feature boundary, a pixel signal line solely representing a non-feature area or a feature may be "flat", with no significant difference in the first and second parts of the signal line. Since the detector may scan from a non-feature area to a feature area or, alternatively, from a feature area to a non-feature area, the "background" signal part of a signal line may either be at the beginning of the signal line, or at the end of the line, respectively. In other words when the pixel size (determined by the illumination spot size, scan rate and sample time) is smaller than the feature size, signal lines for feature boundary pixels may be bimodal, whereas signal lines for other pixels are not bimodal and are flat. Further, if a feature boundary spans multiple pixels, each of those pixel signals may be unimodal, having a line of best fit that is sloped along all or most of the pixel width between the beginning and end of the pixel.

Accordingly, the subject methods of determining whether a pixel signal is a signal representing a feature boundary involve evaluating changes in pixel signal amplitude over the time of the pixel. Several different methods may be used to evaluate amplitude changes of a pixel signal to determine if the pixel is a feature boundary pixel. In certain exemplary embodiments, these methods generally involve evaluating any difference in amplitude between a first part of a pixel signal line (i.e. a signal line representing a signal for a pixel) and a second part of that signal line, to provide an evaluation of amplitude change of the pixel signal line. In other exemplary embodiments, changes in pixel signal amplitude may be evaluated by determining a line of best fit (e.g., a linear or quadratic line of best fit normalized to the median sample) for the pixel signal. In general, a pixel signal having a line of best fit having a slope larger than a certain threshold slope indicates that pixel is a feature boundary pixel.

The above-described methods may generally be used for identifying a signal that is a "feature boundary pixel signal", where a "feature boundary pixel signal" is a signal from pixel at the boundary of a feature. Such signals generally have a significant change in amplitude over the time of the pixel. For example, a feature boundary pixel may have a signal line comprising two consecutive parts, a first part representing a signal from a feature and a second part representing a signal from a non-feature area, or a significant slope. The first and second parts of a pixel signal may be in any order. In certain embodiments, an area of an array corresponding to a pixel is scanned to provide a pixel signal, and any differences in amplitude of the pixel signal (e.g., between the first and second parts of the signal) are evaluated. A significant difference (either an increase or a decrease) in signal amplitude indicates that the pixel signal is a feature boundary pixel signal.

The above-described methods find use in methods of obtaining or processing data from a chemical array. In certain embodiments, an entire signal for a pixel is integrated to provide a single numerical evaluation of the amount of light signal emitted from an area of a chemical array. Accordingly, for a feature boundary pixel signal, background signal as well as feature signal may be integrated together, providing a single evaluation that does not accurately represent the signal for the feature represented in the pixel. Using the above-described methods, a pixel signal that is a feature boundary pixel signal may be detected, the pixel signal may be integrated to provide a numerical evaluation of the pixel, and the numerical evaluation may be adjusted (i.e., increased or decrease) (e.g., according to the difference in amplitude between the first and second parts of the pixel signal line or by ignoring signal that is not feature area derived) to provide a more accurate evaluation of the pixel signal. In certain embodiments the sample number at which the signal passes through the middle of the low and high range (thus transitioning from background to feature) could be linked to the numerical evaluation and the background or feature signal may be defined by the samples that lie on either side of the transition sample). The number of the transition sample may be recorded as an annotation associated with an output data file that may be used during feature extraction. The number could either be encoded into unused bits in the pixel data word, or saved in a separate file.

In performing the above-described methods, a pixel signal is in certain embodiments evaluated to provide a numerical evaluation, of amplitude change using the methods described above. This numerical evaluation may be stored in a data file on a computer readable medium, and may be used at a later date. In certain embodiments, a pixel signal may also be integrated to provide a numerical evaluation of the pixel (i.e., an evaluation of the brightness of the pixel). This numerical evaluation may also be stored in a data file on a computer readable medium, and may be used at a later date.

In certain embodiments, such a processor may have two outputs, one output representing the evaluation and one output representing the amplitude change evaluation of the pixel. However, in other embodiments, a processor may have a single output (e.g., a binary number of the like) that represents both the evaluation and the amplitude change of the pixel. For example, if a processor with a 16-bit, 24-bit, 32-bit or greater than 32-bit (e.g., 64-bit or greater, etc.) word size is used, a plurality of the bits, usually at least 12 bits (e.g., at least 14, 16, 20, 24, or more bits) are used to represent the pixel evaluation, whereas the remainder or a portion of the remainder of bits (usually at least 2, 4, 6, or 8 or more, usually up to about 12 or more bits) are used to represent the amplitude change. Other information that could be associated with the numerical assessment includes: a) an indication of which end of the pixel (e.g., the "left" or "right" end) represents signal from background or feature (e.g., an indication of whether the pixel has a rising or falling transition), b) an indication of the percentage change of the feature, and c) an indication of how far through the pixel transition (from low to high or from high to low) is observed. For example, i.e. if a low signal has an amplitude of 1 and a high signal has an amplitude of 3 and there are 100 samples, the sample at which the signal transition from below 2 to above 2 may be recorded.

The processor output for a single pixel may be used by data extraction or analysis software to identify integrated signals corresponding to feature boundary pixel signals, or to adjust an evaluation of the pixel to provide a more accurate evaluation of the brightness of the pixel, as described above.

Without wishing to limit the invention to any particular embodiment and with reference to FIG. 1, this embodiment of the invention will be described in greater detail below.

Graph 2 of FIG. 1 shows a representative signal line for a feature boundary pixel (i.e., a representative signal line for a pixel representing a feature boundary), where t is time, and i is signal amplitude. In this example, the first part of the signal line 6 represents signal from a non-feature area (i.e., background signal) whereas the second part of the signal line 4 represents signal from a light-emitting feature. In certain embodiments, and as described in greater detail in previous sections of this disclosure, such a signal line is an analog signal line that is usually the output of a detector (or a processed version thereof) that has passed over (i.e., scanned) the edge of a feature.

In certain embodiments, this signal line is sampled and digitized by an analog-to-digital converter, to provide a plurality of digital signals for said pixel 8. These signals are input into a digital signal processor in which certain embodiments of the invention are performed.

In certain embodiments, the processor, as described above, evaluates amplitude change of the pixel signal 14. This evaluation may be done using straightforward or more complex methods, depending on the speed of the processor used and the desired outcome.

In a simple case, amplitude change may be evaluated by determining the percent increase or decrease in the intensity of the first and second halves of a pixel signal relative to its average intensity. In other words, the first half of a pixel signal may be averaged (e.g., to produce signal line 12) the second half of a pixel signal may be averaged (e.g., to produce signal line 10) and those averages compared to the average intensity for the entire pixel signal, to provide an evaluation of the change in intensity of the pixel signal. More complex methods may involve first analyzing a pixel signal line with graphing software to determine if the signal line has two proximal plateaus of different amplitude (e.g., is a signal line that can be described by a step function, e.g., a bimodal line) and, if such a signal line is detected, then comparing the signal amplitudes of the two plateaus and providing a numerical evaluation of the amplitude difference. In other embodiments, a bimodal pixel may be identified by calculating the means and standard deviations of the first half and second half of a pixel. A pixel is likely a feature boundary pixel if the difference between the means is large compared to their combined standard deviation. In other embodiments, a pulse height analyzer may be employed to generate a histogram of sample values, and identify peaks in the histogram.

As mentioned above, in other exemplary embodiments, changes in pixel signal amplitude may be evaluated by determining a line of best fit (e.g., a linear or quadratic line of best fit normalized to the median sample) for the pixel signal. In general, a pixel signal having a line of best fit having a slope larger than a certain threshold slope indicates that pixel is a feature boundary pixel. In these embodiments, the pixel signal may be further evaluated to determine the fit of the signal to the line of best fit. For example, the root mean square deviation from the fit could be calculated. In general, a feature boundary pixel is indicated if a pixel is a good fit to its line of best fit and its line of best fit has a significant slope (a slope greater than a pre-determined threshold slope, for example). These methods are particularly employable when the resolution of the scanner being used is approximately comparable to the pixel size so that the signal will likely change over most of the pixel width.

In general, with any of the methods discussed above, the significance of a change in amplitude of a pixel signal may vary for each scanner system used (because of the resolution of the scanner and feature size, etc.). However, the significance of a change in amplitude of a pixel signal and may experimentally determined, for each scanner system, by routine methods. For example, a scanner may be trained to recognize the shape of feature boundary pixels by scanning a feature boundary to provide a feature boundary pixel signal, and training the scanner to recognize the shape of that type of pixel signal.

As discussed above, methods of evaluating amplitude change of a pixel signal find use in a variety of applications. For example, such methods may be used to detect feature boundary pixel signals and thereby provide information about (e.g., indicate the position of) feature boundaries 16 in a scan of an biopolymeric array. Used with data extraction software, this feature boundary information may be used to extract data only from pixels representing features and not, for example, non-feature areas.

In one embodiment, to detect a feature boundary pixel signal, amplitude change of a pixel signal is evaluated to determine if the change is significant. A significant change in amplitude usually indicates a feature boundary pixel signal. What constitutes a "significant" or "insignificant" change in signal intensity may easily be determined empirically. In certain embodiments, however, pixels with a "significant" difference those with a pixel difference over a threshold, usually a pre-determined threshold, and may be pixel signals that have a greater than about two-fold (e.g., a greater than 3, 4, 5, 10, 20, 50 or 100-fold or more, usually up to about 1000-fold or more) increase or decrease in signal intensity, as compared to a pixel with no increase in signal intensity (e.g., a flat line signal).

In another embodiment, a "significant" difference is one which is greater than about 10%, greater than about 20%, greater than about 30%, greater than about 40%, greater than about 50%, greater than about 60%, greater than about 70%, greater than about 80%, greater than about 90%, or greater than about 100% increase or decrease in signal. In a further embodiment, a "significant" difference is one which is statistically significant ($p<0.5$). In cases where the pixel signal line is flat, and depending on the exact method used for evaluation, the evaluation will be usually show that the change in signal intensity is not significant.

The subject methods of numerically evaluating signal amplitude change of a feature boundary pixel signal may also be used in methods of adjusting (i.e., changing or correcting) a numerical evaluation of the signal amplitude of a pixel to provide a more accurate evaluation of the brightness of a pixel 18. Again, these methods may be performed using straightforward or more complex protocols, depending on the desired result. For example, in the example set forth above, where the amplitude change may be evaluated by determining the percent increase or decrease in the intensity of the first and second parts of a pixel signal relative to its average intensity, the numerical evaluation of the pixel may be adjusted in proportion to the calculated increase or decrease. For example, if the percent increase or decrease is a certain percentage, e.g., a 1000% increase, then the numerical evaluation may be multiplied by a factor proportional to that percentage. In this case, since the first and second halves of the signal line were compared to provide the percentage increase or decrease, the numerical evaluation may be increased by 500% (half of 1000%), i.e., multiplied by a factor of 5, to provide an adjusted numerical evaluation that more accurately reflects the brightness of the pixel. Again, more complex methods may be used to adjust a numerical evaluation of the signal amplitude of a pixel based on signal amplitude changes of a pixel signal, and these may generally involve standard graphing and extrapolation tools. In one embodiment, if two proximal plateaus of different amplitude are detected in a pixel signal line (e.g., having two plateaus similar to the signal line shown in graph 2 of FIG. 3), then the higher plateau signal may be extrapolated to encompass the entire pixel, and the entire signal (i.e., the higher plateau signal line and the extrapolated signal line) may be integrated to provide an adjusted numerical evaluation of the pixel that more accurately represents the brightness of the pixel. Alternatively, the samples representing the lower plateau may be ignored during integration.

As would be recognized by one of skill in the art, many of the methods described above may be performed after a pixel has been integrated. In other words, the feature boundary signal pixel detection methods and the numerical evaluation adjustment methods described above may be performed after the pixel signal is integrated. For example, a numerical evaluation of a pixel may be tagged or associated with an adjustment factor as the numerical evaluation is output from the processor, and any adjustments of the numerical evaluation may done at a later time, by analysis software, for example. Accordingly, a pixel signal may be assessed by a scanner using the methods described above to produce data, the data may be exported from the scanner and optionally stored, and a second computer may identify feature boundaries and/or adjust pixel evaluations for feature boundary pixel signals, according to the methods described above.

In certain embodiments, the subject methods may be done in "real-time". In other words, an integrated signal (i.e. an "evaluation" of the pixel) and an evaluation of amplitude change of the signal (i.e., an "amplitude change evaluation" of the pixel) are generally output from a single processor prior to processing the signal for the next pixel. In a particular embodiments however, data obtained from a signal may be stored in a buffer and analyzed while accumulating data from a future pixel, e.g., the next pixel scanned.

Computer-Related Embodiments

The invention also provides a variety of computer-related embodiments. Specifically, the methods described above may be in the form of programming for execution by a digital system processor. Accordingly, the invention provides a digital signal processor programmed to evaluate pixel signal amplitude change and/or identify feature boundary pixels, as described above. The programming may be coded onto computer-readable medium, and the programming and the processor may be part of a computer based system.

The invention also provides feature extraction and data analysis software that uses the methods for identifying feature boundary pixels described above. Such software may use the information provided by the methods described above to identify and extract data from pixels that contain only feature information, and may, in some embodiments, alter data for feature boundary pixels using the methods described above. Feature extraction describes the method by which numerical data is obtained from an array. In general feature extraction methods involve identifying a feature (usually corresponding to a probe) on a scan of a hybridized array, and measuring the amount of label (e.g., fluorescence) that is associated with the feature. In exemplary embodiments, feature extraction methods provide a numerical figure for chosen features in each of the two or more scans of an array. Several commercially available programs perform feature extraction on microarrays, such as IMAGINE™ by BioDiscovery (Marina Del Rey, Calif.) Stanford University's "ScanAlyze" Software package, Microarray Suite of Scanalytics (Fairfax, Va.), "DeArray" (NIH); PATHWAYS™ by Research Genetics (Huntsville, Ala.); GEM tools™ by Incyte Pharmaceuticals, Inc., (Palo Alto, Calif.); Imaging Research (Amersham Pharmacia Biotech, Inc., Piscataway, N.J.); the RESOLVER™ system of Rosetta (Kirkland, Wash.) and the Feature Extraction Software of Agilent Technologies (Palo Alto, Calif.). Such commercially available programs may be readily adapted or modified to perform the subject methods. In certain embodiments, array analysis software may combine the product of the subject methods, e.g., an indication that a certain pixel is a feature boundary pixel, with other information (i.e. topographical boundaries) in order to accurately which pixels represent features and which pixels do not represent features.

In certain embodiments, the above methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory.

Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

Optical Scanners

The subject systems and methods find particular use in chemical, e.g., biopolymeric, array scanners. Accordingly, also provided by the subject invention is a chemical array scanner that contains a system for performing the subject methods described above. Such scanners may have a laser excitation system for emitting light from the surface of a chemical array, hardware for performing the methods described above, and, usually, a storage medium for storing data produced by scanning. A subject scanner may also contain programming for executing the subject methods.

Any optical scanner or device may be provided to include the above programming. Representative optical scanners of interest include those described in U.S. Pat. Nos. 5,585,639; 5,760,951; 5,763,870; 6,084,991; 6,222,664; 6,284,465; 6,329,196; 6,371,370 and 6,406,849—the disclosures of which are herein incorporated by reference. An exemplary optical scanner as may be used in the present invention is shown in FIG. 2.

Figure 2:
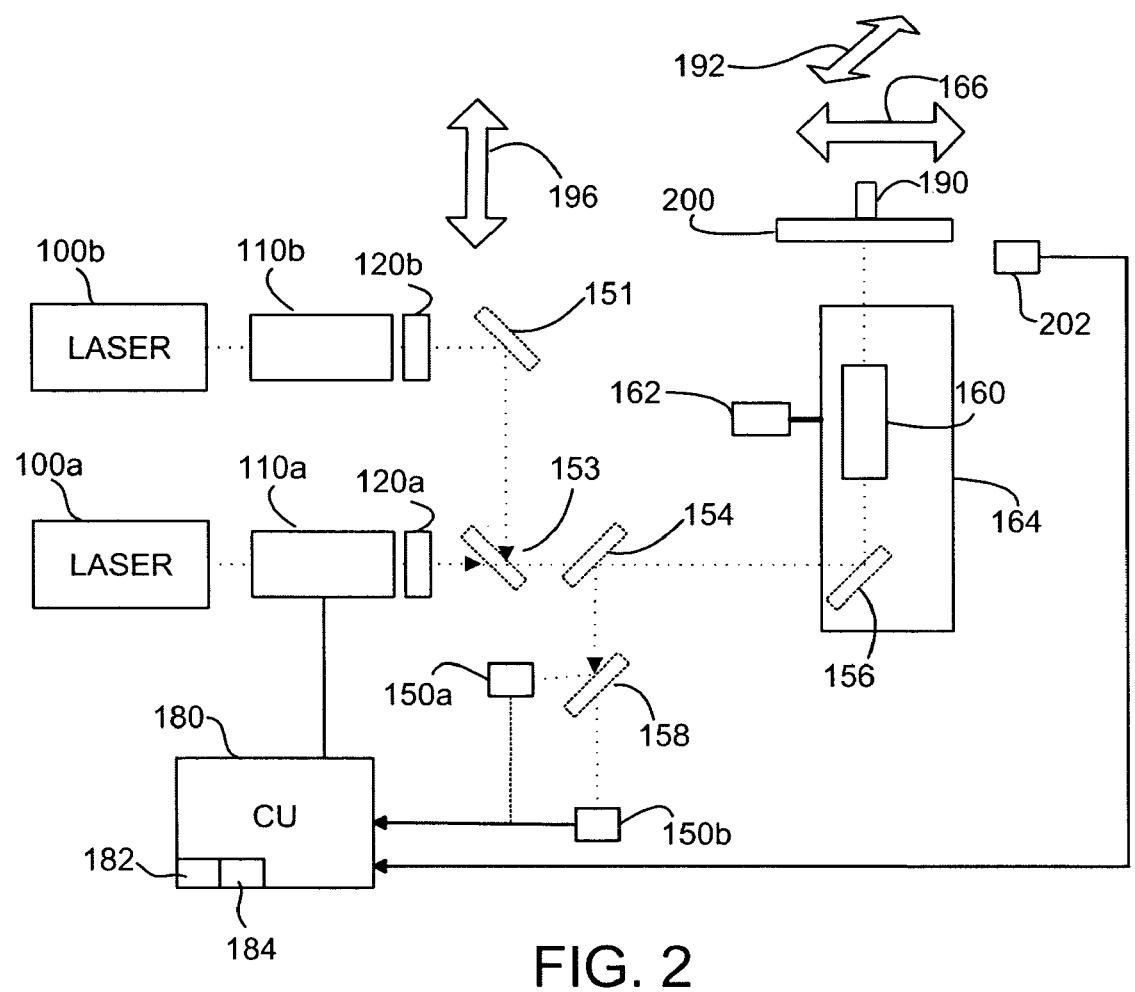
FIG. 2 schematically illustrates an apparatus as may be used in the present invention.

Referring now to FIG. 2, an exemplary apparatus of the present invention (which may be generally referenced as an "array scanner") is illustrated. A light system provides light from a laser 100 which passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. Depending on how the subject methods are implemented, a subject scanner may contain more than one of 150a, and more than one of 150b, or, in alternate embodiments, 150a and 150b may be multi-gain detectors.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT), or photodiode or avalanche photodiode device (APD), such as a charge-coupled device (CCD), a charge-injection device (CID), or a complementary-metal-oxide-semiconductor detector (CMOS) device). All of the optical components through which light emitted from an array or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package mounted on holder 200. The scanned regions for an array will include at least the multiple features of the array. In particular the scanning system may be a line by line scanner, scanning the interrogating light in a line across an array when at the reading position, in a direction of arrow 166, then moving ("transitioning") the interrogating light in a direction into/out of the paper as viewed in FIG. 2 to a position at an end of a next line, and repeating the line scanning and transitioning until the entire array has been scanned.

This scanning feature is accomplished by providing a housing 164 containing mirror 158 and focuser 160, which housing 164 can be moved along a line of pixels (i.e., from left to right or the reverse as viewed in FIG. 2) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 2 may further include a reader (not shown) which reads an identifier from an array package. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

The system may also include detector 202, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, autofocus system 202 may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150a, 150b (these different signals being different "channels"), namely a signal which results at each of the multiple detected wavelengths from emitted light for each scanned region of array 12 when at the reading position mounted in holder 200. Controller 180 also receives the signal from autofocus detector 202, and provides the control signal to EOM 110, and controls the scan system. Controller 180 contains all the necessary software to detect signals from detector 202, and regulate a motorized or servo-controlled adjuster 190 through a control loop. Controller 180 may also analyze, store, and/or output data relating to emitted signals received from detectors 150a, 150b in a known manner.

Controller 180 also includes a programmable digital signal processor for performing the methods described above. In certain embodiments, controller 180 includes plurality of analog-to-digital converters, and other components of a multi-gain photodetection system, e.g., a current-to-voltage converter, voltage amplifier, etc., as desired, a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

The saved results from a sample exposed array, read with the methods described above, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

While it is noted that a scanner that reverses scanning direction at the end of each scan line (i.e. a bi-directional scanner) is disclosed, unidirectional scanners also find use with the methods of the invention.

Utility

The subject array scanners find use in a variety applications, where such applications are generally analyte detection applications in which the presence of a particular analyte in a given sample is detected at least qualitatively, if not quantitatively.

Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. Certain embodiments of the invention may involve transmitting data obtained from a method described above from a first location to a remote location. Certain other embodiments of the invention may involve receiving, from a remote location, data obtained from a method described above.

In reading the array, pixel signals are usually processed using the methods described above.

It is further noted that aspects of the invention may be applicable to a variety of optical scanners including those that detect chemiluminescent or electroluminescent labels. The present invention will be applicable to such scanners where powering down the scanner will result in lifetime savings, as exemplified above.

Kits

Kits for use in connection with the subject invention may also be provided. Such kits usually include at least a computer readable medium including computer program product comprising, as discussed above, a processor programmed to perform the above-methods, and/or, in certain kits, instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject programming and instructions, the kits may also include one or more reference arrays, e.g., two or more reference arrays for use in testing an optical scanner after software installation.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A computer-implemented method of determining whether a pixel signal produced during scanning of a chemical array is a feature boundary pixel signal, wherein said pixel signal is produced by a chemical array scanner, comprising:
    evaluating change in amplitude within a signal for a single pixel;
    indicating said pixel as a feature boundary pixel if said signal has a significant change in amplitude;
    integrating said signal to produce data; and
    storing said data on a permanent memory of a computer implementing said computer-implemented method.

2. The method of claim 1, wherein said array is a nucleic acid array.

3. The method of claim 1, wherein said array is a polypeptide array.

4. The method of claim 3, wherein a pixel signal having a change in amplitude above a pre-determined level indicates that said signal is a feature boundary pixel signal.

5. The method of claim 1, wherein said method comprises evaluating any difference in amplitude between a first part of said signal and a second part of said signal to provide an evaluation of amplitude change of said pixel.

6. The method of claim 1, wherein a pixel signal having a line of best fit having a slope greater than a threshold slope indicates that said pixel is a feature boundary pixel.

7. The method of claim 6, wherein said method comprises evaluating closeness of said pixel signal to its line of best fit.

8. The method of claim 1, wherein said evaluating provides a numerical evaluation.

9. The method of claim 1, wherein said integrating produces a numerical evaluation of said pixel.

10. The method of claim 9, comprising storing said numerical evaluation on a computer readable medium.

11. The method of claim 9, wherein said numerical evaluation of said pixel is adjusted if said pixel is a feature boundary pixel.

12. The method of claim 9 wherein said numerical evaluation is annotated with information indicating an adjustment factor for adjusting said numerical evaluation if the pixel is a feature boundary pixel.

13. The method of claim 1, wherein said method further comprises indicating which end of said pixel signal represents signal from a feature area or which end of said pixel signal represents signal from a non-feature area if said pixel is a feature boundary pixel.

14. The method of claim 1, wherein said method further comprises indicating where in said pixel signal transition between signal from a feature area and signal from a non-feature area is if said pixel is a feature boundary pixel.

15. The method of claim 1, further comprising scanning a chemical array to provide said pixel signal.

16. A chemical array scanner comprising:
   a laser excitation system;
   a photodetection system that produces a signal representative of emitted light from the surface of an array;
   and a computer comprising instructions for performing the method of claim 1.

17. The chemical array scanner of claim 16, further comprising a storage medium for storing data.

18. The chemical array scanner of claim 16, wherein said emitted light from the surface of an array is fluorescent light.

19. A non-transitory computer-readable medium comprising:
   programming for execution by a digital signal processor to produce data for a pixel in a scan of a chemical array, wherein said programming comprises the following instructions:
   evaluating change in amplitude within a signal for a single pixel;
   indicating said pixel as a feature boundary pixel if said signal has a significant change in amplitude;
   and integrating said signal to produce data.

20. The computer-readable medium of claim 19, wherein the further comprising instructions to provide an output as a multi-bit code, in which a first part of said code represents an evaluation of amplitude of said signal and a second part of said code represents said integrated signal.

21. A computer comprising a processor and the computer-readable medium of claim 19.

* * * * *